United States Patent
Fahy et al.

(10) Patent No.: US 6,616,858 B2
(45) Date of Patent: Sep. 9, 2003

(54) PREVENTION OF ICE NUCLEATION BY POLYGLYCEROL

(76) Inventors: Greg Fahy, 880 Via Blairo, Corona, CA (US) 92879; Brian Wowk, 848 Montague Dr., Corona, CA (US) 92879

(*) Notice: Subject to any disclaimer, the term of this patent is extended or adjusted under 35 U.S.C. 154(b) by 0 days.

(21) Appl. No.: 09/726,857

(22) Filed: Nov. 30, 2000

(65) Prior Publication Data

US 2002/0063235 A1 May 30, 2002

Related U.S. Application Data

(60) Provisional application No. 60/167,963, filed on Nov. 30, 1999.

(51) Int. Cl.[7] .............................. C09K 3/18; A01N 1/00; A01N 1/02
(52) U.S. Cl. ................................ 252/70; 47/2; 106/13; 252/71; 252/73; 252/77; 435/1.1; 435/1.3; 435/260
(58) Field of Search .............................. 252/70, 71, 73, 252/77; 106/13; 47/2; 435/1.1, 1.3, 260

(56) References Cited

U.S. PATENT DOCUMENTS

| | | | | |
|---|---|---|---|---|
| 2,373,727 A | * | 4/1945 | West et al. ............... | 106/13 |
| 3,968,169 A | * | 7/1976 | Seiden et al. ............ | 549/347 |
| 4,077,895 A | | 3/1978 | Langdon et al. .......... | 252/76 |
| 4,388,203 A | | 6/1983 | Nimerick et al. ......... | 252/70 |
| 4,565,643 A | | 1/1986 | Arai et al. ............... | 252/70 |
| 5,104,415 A | * | 4/1992 | Koci ........................ | 8/527 |
| 5,710,350 A | * | 1/1998 | Jeromin et al. ........... | 568/868 |
| 5,904,944 A | | 5/1999 | Battermann et al. ...... | 426/281 |
| 5,952,168 A | | 9/1999 | Wowk et al. .............. | 435/1.3 |

FOREIGN PATENT DOCUMENTS

| | | | |
|---|---|---|---|
| DE | 2127680 | * | 4/1971 |
| EP | 0 291 073 | | 11/1988 |
| WO | WO 97/16062 | | 5/1997 |

OTHER PUBLICATIONS

Database WPI, XP–002172967 (abstract of Japanese Patent Specification 58–91775 (5/83).

* cited by examiner

*Primary Examiner*—Anthony J. Green
(74) *Attorney, Agent, or Firm*—Foley & Lardner

(57) ABSTRACT

Linear polymers of glycerol can prevent or delay ice nucleation in a variety of contexts. Polyglycerol can also be employed in combination with other ice control agents, such as polyvinyl alcohol/polyvinyl acetate copolymers and antifreeze proteins, to provide antinucleation effects that are superior to those of either polyglycerol or the co-antinucleator alone. Polyglycerol has a number of advantageous physical and toxicological properties, such as extreme water solubility, non-toxicity to human beings, non-toxicity to animal tissues and organs in vitro even at extreme concentrations, minimal foaming tendency, minimal retention on hydrophobic surfaces, and stability in solution without the need for periodic heating to reactivate its antinucleation properties.

29 Claims, 12 Drawing Sheets

PREVENTION OF ICE NUCLEATION BY POLYGLYCEROL

RELATED APPLICATIONS

This application is related to U.S. provisional patent application No. 60/167,963, filed Nov. 30, 1999, from which priority is claimed.

FIELD OF THE INVENTION

This invention relates to methods of inhibiting ice formation using polyglycerol and related molecules.

BACKGROUND OF THE INVENTION

Preventing the freezing of water, and solutions that contain water, is a problem of substantial environmental, agricultural, industrial, and biomedical interest. Ice on walkways, roads and aircraft wings constitutes an environmental hazard to transportation. Ice formation on and inside plants causes expensive damage to crops and gardens. Freezing of antifreeze solutions, pipeline contents, paints, wet concrete and other aqueous solutions subjected to cold temperatures are issues of concern for industry. Avoiding ice formation during cold storage of proteins, viruses, cells, tissues, and organs is an important problem in cryobiology.

Below a critical temperature (the equilibrium freezing point), the crystallization of water into ice becomes thermodynamically favored. The equilibrium freezing point of water can be lowered by adding solutes that lower the vapor pressure of water such that it becomes equivalent to the vapor pressure of ice only at a lower temperature. This classical means of freezing point depression is termed "colligative" freezing point depression, and is approximately independent of the nature of the added solute, the effect being proportional instead to the mole fraction of the added solute regardless of its nature. Colligative freezing point depression is the physical basis on which essentially all currently used antifreeze agents (such as glycols and salts) operate. The disadvantage of colligative freezing point depression is that large quantities of solutes (10% or more) are required to lower the freezing point by even a few degrees Celsius.

Beyond colligative freezing point depression, there are two independent means of lowering the practical freezing point of water. The first is to inactivate heterogeneous nucleating agents, and the second is to inhibit growth of small ice crystals despite cooling to below the equilibrium freezing point.

Pure water freezes spontaneously (homogeneous nucleation) at just above −40° C. when ice is not previously nucleated by impurities in the water known generically as heterogeneous nucleating agents. Biogenic heterogeneous nucleating agents are often simply called ice nucleating agents (INAs). Biogenic INAs have apparently evolved to reduce or eliminate supercooling in a variety of contexts, but minerals and organic nucleators also exist. Even highly purified laboratory grade water retains significant nucleation tendency. If INAs can be removed or inhibited, water and water solutions can be supercooled to temperatures many degrees below the freezing point without actually freezing.

Cold-hardy plants, insects, and fish have evolved antifreeze proteins that selectively adsorb onto the surface of ice or INAs, thereby preventing water molecules from coming into contact with surfaces that trigger ice growth (Devries, A. L., and Wohlschlag, D. E. "Freezing resistance in some Antarctic fishes" Science 163, pp. 1074–1075, 1969). Antifreeze proteins thus act as non-colligative antifreeze agents, and very small concentrations (less than 1%) are able to suppress the temperature at which ice forms, in some cases by several degrees. Soon after the original discovery of antifreeze proteins, it was speculated that "many polymeric molecules (not just proteins) ought to be able to inhibit nucleation (of ice) in this way" (Klotz, I. M. in "The Frozen Cell" pp. 5–26. J. & A. Churchill, London, 1970). These speculations opened the door to the possibility that inexpensive synthetic compounds might be found with non-colligative antifreeze activity.

In 1983, Caple et al ("Polymeric Inhibition of Ice Nuclei Active Sites" Cryo-Letters 4, pp. 51–58, 1983 and U.S. Pat. No. 4,484,409) reported significant enhancement of water supercooling tendency by adding small quantities of methyl acrylate-co-vinyl pyrrolidone polymer or methyl methacrylate-co-vinyl pyrrolidone polymer. While showing proof of concept, these observations were limited in a number of important respects. First, these copolymers were not tested for toxicity and may be toxic. Second, release of these polymers into the environment, or their inclusion in foods, may not be permissible. Third, the polymers required substantial hydrophobicity for effectiveness, which limits their utility in water solutions. Fourth, the nature of these polymers and of the methods for their synthesis may make them too expensive for practical use. Finally, their performance was not fully characterized, and may be limited in a variety of ways. In any case, no commercial use of Caple's polymers has appeared in the 16 years since their publication, implying unreported deficiencies of these polymers for practical ice antinucleation applications. Similarly, the Japanese investigators Watanabe et al. showed that they could reduce nucleation by silver iodide using an NMR assay method by reacting proteins with hydrophobic aliphatic chains of varying lengths (US Patent Application, recently lapsed). But this method appeared to require the resulting modified proteins to form micelles in order to gain the antinucleation activity reported, a factor that will limit the accessibility of the antinucleators to nucleating bodies in general, and that may prevent the invention from being used in organ perfusion applications wherein the micelles may not penetrate through capillaries into the interstitial space. In any case, no industrial use of their invention is known, and the US rights to their invention recently lapsed due to non-payment of maintenance fees by the assignee, implying a lack of utility. A variety of other antinucleation substances has been described, but these are generally either chemically reactive substances that destroy ice nucleators and would be expected to also damage vital biomolecules present in cells or the environment, or are complicated organic chains that may have unacceptable toxicity and chemical reactivity and that tend to be hydrophobic and otherwise difficult or problematic to use.

In 1995, Fahy ("Novel Ice-Controlling Molecules and Their Applications" International Patent Application PCT/U.S.96/04284, Publication # WO 96/30459, 1996, superceded by PCT application PCT/U.S.98/20834, Publication # WO 99/18169, published on Apr. 15, 1999) proposed creating synthetic ice interface dopants ("ice blockers") specifically designed to bind to the basal plane and prism faces of ice crystals (and ice nucleators). Molecules were to be designed by spacing polar groups at intervals corresponding to the lattice spacing of water molecules on the crystal faces of ice. Numerous specific molecules and polymers were proposed, and data were presented showing reduction of ice crystal growth rates by 6% w/v 1,3-cis-cyclohexanediol and augmentation of the thermal hysteresis effect of fish antifreeze glycoprotein by 1,3,5-cis,cis-cyclohexanetriol, but the latter effect was said to be impossible to utilize due to the pro-nucleating effect of 1,3,5-cis,cis-cyclohexanediol. Also, no data were shown indicating thermal hysteresis augmentation by any other agent, nor confirming any ice-bonding effect of 1,3-cis-cyclohexanediol or any other proposed agent.

Claims were presented for several specific polymers as agents for inhibiting ice crystal growth, but none of these polymers was shown to inhibit ice crystal growth, and none anticipated either the polyvinylacetate/polyvinylalcohol (PVA) antinucleating copolymers of Wowk (U.S. patent application Ser. No. 09/400,791) or the novel antinucleating species disclosed herein.

At sufficiently high concentrations (typically 50% or more), conventional colligative antifreeze agents can prevent ice formation completely, allowing aqueous solutions to be cooled to arbitrarily low temperatures without freezing. In the field of cryobiology, this is the basis of cryopreservation by vitrification (Fahy, G. M. et al "Vitrification as an approach to cryopreservation" Cryobiology 21, pp. 407–426, 1984). However the utility of vitrification is currently limited by the toxicity of the high colligative cryoprotectant concentrations required to achieve vitrification. Cryopreservation by vitrification would be more practical for a wider variety of cell and tissue types if means could be found for lowering the colligative cryoprotectant concentrations required to achieve vitrification.

In 1990, it was proposed that fish antifreeze proteins might be useful as inhibitors of background INAs in vitrification solutions (Fahy, G. M., Saur, J., and Williams, R. J. "Physical problems with the vitrification of large biological systems" Cryobiology 27, pp. 492–510, 1990). Inhibition of INAs would allow lower concentrations of cryoprotectants to be used for vitrification, particularly for vitrification of large systems for which discrete ice nucleating events caused by background INAs is a greater problem due to the slower cooling and warming rates that are achievable for larger systems. The Fahy proposal was subsequently validated when Sutton and Pegg achieved a spectacular decrease in the critical warming rate necessary to avoid ice formation in vitrified solutions by adding 1% fish antifreeze protein ("Devitrification in Butane-2,3-diol Solutions Containing Anti-Freeze Peptide" Cryo-Letters 14, pp. 13–20, 1993). The value of non-colligative antifreeze agents for enhancing vitrification solutions was becoming clearer. However until the discovery of the ice-inhibitory effects of PVA and the molecules of the present invention there have been no low cost INA-inhibiting agents readily available.

Prevention of ice formation clearly has application in any situation in which ice formation has adverse or undesired consequences. Hence, the utility of the present invention is expected to be very broad.

BRIEF DESCRIPTION OF THE DRAWINGS

These and other features, aspects and advantages of the present invention will now be described with reference to the drawings of the preferred embodiment, which embodiment is intended to illustrate and not to limit the invention, and in which.

SUMMARY OF THE INVENTION

Figure 1:
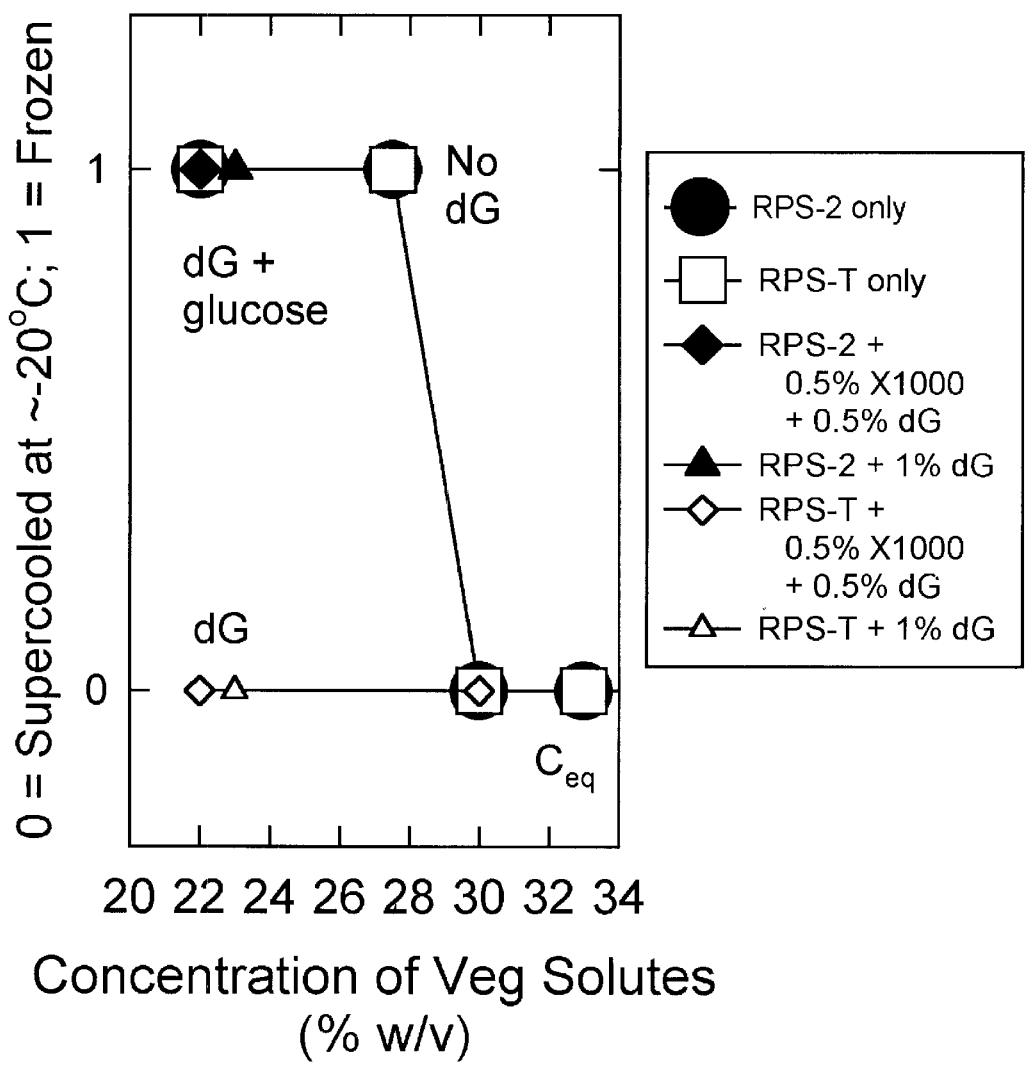
FIG. 1 shows the CPA concentration needed for stable supercooling at about −20° C. using Decaglycerol (dG) and dG+X1000.

It is the object of the present invention to provide compounds that non-colligatively suppress ice nucleation while retaining desirable physical, biological, and industrial properties.

It is a further object of the invention to provide additives that complement other ice nucleation inhibitors, especially polyvinylacetate/polyvinylalcohol copolymers.

It is a further object of the invention to provide additives that complement or augment the thermal hysteresis and antinucleation effects of natural antifreeze proteins.

It is a further object of the invention to provide additives that reduce ice nucleation in dilute aqueous solutions, in concentrated cryoprotectant solutions, and in commercial antifreeze preparations.

It is a further object of the invention to provide additives that are so nontoxic as to be useful in organ preservation solutions as impermeant solutes capable of preventing cell swelling over periods of several days near or below zero degrees Celsius with excellent maintenance of cellular viability.

It is a further object of the invention to provide additives that are sufficiently nontoxic to facilitate hypothermic preservation of biological materials in a supercooled state below 0° C.

It is another object of the invention to provide compounds that adsorb onto ice nucleating agents for purposes of extracting ice nucleating agents from water and water solutions.

It is a further object of the invention to provide additives that are compatible with perfusional preservation of organs, especially for inclusion in vitrifiable perfusates.

It is still another object of the invention to provide compounds that may be dispersed in the atmosphere to alter precipitation in rain clouds by inhibiting atmospheric ice nucleating agents.

These and other objects of the present invention will be apparent to those of ordinary skill in the art in light of the description below and appended claims.

DETAILED DESCRIPTION OF THE PREFERRED EMBODIMENT

"Polyglycerol (PGL) is a water-soluble polymer given by the formula $H[-OCH_2CHOHCH_2-]_nOH$. PGL is commercially available with n=2 (diglycerol) (about 166 Daltons) up to n=10 (decaglycerol) (about 758 Daltons) and beyond. For tetraglycerol, n=4 (about 314 Daltons), and for hexaglycerol, n=6 (about 462 Daltons)."

The previously-unknown utility of various varieties of PGL for preventing nucleation and enhancing supercooling of water is herein disclosed. One theory for the utility is that the compound may preferentially adsorb onto ice nucleating particles and surfaces in a manner analogous to natural antifreeze proteins. As the data below show, very small concentrations of PGL (as little as 10 parts per million) significantly enhance the ability of water and water solutions to supercool without ice formation. PGL is effective alone, in combination with PVA, and in combination with natural antifreeze proteins.

"PGL is detectably effective as an ice inhibiting agent at concentrations ranging from 10 parts per million to tens of percent. Concentrations ranging from 0.01% to 10% are preferred. Concentrations ranging from 0.1% to 3% are more preferred. Concentrations ranging from 0.3% to 2% are most preferred. It will be understood by those skilled in the art that the choice of PGL concentration in any antifreeze application will also depend on factors other than maximum ice inhibition, including cost and solution viscosity considerations."

"Tetraglycerol, hexaglycerol, and decaglycerol were all found to be useful, with good ice blocking activity (antinucleation), low viscosity, lack of foaming and plastic-wetting properties in dilute aqueous solution (hence ease of pipetting), and absence of the clouding seen in PVA. (In the case of PVA, heating is needed to reverse clouding prior to use to reactivate antinucleation tendency.) Decaglycerol may be slightly superior to lower chain length variants of PGL as an antinucleator in some cases, although in other cases tetraglycerol has seemed slightly superior. We anticipate that PGL will be active as an antinucleator for n=2, n=3, n=5, n=7–9, and n>10, for example n=11–1000 (i.e. 832 Daltons to 74,018 Daltons)."

The activity of at least some kinds antifreeze protein molecules can be enhanced by complexing them with or exposing them to other molecules, such as antibodies (Wu, D. W., Duman, J. G., and Xu, L. "Enhancement of insect antifreeze protein activity by antibodies" Biochim Biophys Acta 1076, pp. 416–420, 1991—herein incorporated in its entirety by reference thereto) and small bivalent solutes such as citric acid and glycerol. It is reported herein that decaglycerol (dG) also greatly activates the practical activity of recombinant Dendroides antifreeze protein 1, increasing its thermal hysteresis (defined below) as determined in a cryomicroscope from about 0.3–1.5 degrees C. without dG to 3.5 degrees in the presence of dG. Decaglycerol may act to prevent new ice nucleation events in the deeply supercooled environment that otherwise lead to ice formation more rapidly than antifreeze proteins can attach to the new ice, which outstrips the ability of the protein to control pre-existing ice.

The increase in activity of antifreeze proteins as noted above may be due to an increase in the area of ice that is effectively covered by the protein-solute complex. It is therefore anticipated that the ice blocking activity of PGL compounds can also be further enhanced by adding molecular appendages that increase the lateral extent of the molecule when it is bound to an ice nucleating surface. A portion of the hydroxyl groups in PGL (preferably not exceeding 20% of the total number of hydroxyls) can be easily converted into ester or ether linkages for connecting these appendages.

PGL is effective at inhibiting ice nucleation caused by a bacterial INA. This demonstration is significant because ice nucleating proteins of bacterial origin are believed to be a major source of background INAs in the environment. In particular, ice nucleating bacteria such as *Pseudomonas syringae* and *Erwinia herbicola* present on plant surfaces are believed to be the primary cause of plant frost damage at temperatures between –6° C. and 0° C.

Various prior art methods have been proposed to control ice nucleating bacteria on plants at risk of frost damage. These methods include applying bactericide (U.S. Pat. Nos. 4,834,899 and 5,079,868—herein incorporated in its entirety by reference thereto), bacteriophages (U.S. Pat. No. 4,375,734—herein incorporated in its entirety by reference thereto) and displacing INA bacteria with similar bacteria that don't produce INA proteins (U.S. Pat. Nos. 4,045,910/4,161,084/4,432,160—herein incorporated in its entirety by reference thereto). The methods most similar to the present invention are proposals to spray solutions containing natural (U.S. Pat. No. 4,601,842—herein incorporated in its entirety by reference thereto) or synthetic (U.S. Pat. No. 4,484,409—herein incorporated in its entirety by reference thereto) ice nucleation inhibiting compounds onto plants. The present invention is superior to these inventions because PGL compounds are much less expensive than natural antifreeze proteins, and because PGL compounds are known to be non-toxic unlike the polymers of U.S. Pat. No. 4,484,409.

Many possible embodiments of the present invention for protecting plants against freezing damage will be apparent to those skilled in the art. In one embodiment, PGL compounds can be included in water sprays that are used to spray the surface of plants at acute risk of freezing. In another embodiment, PGL compounds can be included in normal irrigation water on a long-term basis. Only very small concentrations would be necessary because evaporation would concentrate the compound on plant surfaces. In another embodiment, low molecular weight PGL compounds might be included in irrigation water, fertilizer formulations, or plant potting soil so that these compounds are absorbed by plants to provide freezing protection inside plant tissues. In another embodiment, PGL compounds might be dispersed in the form of a powder on plants. In still another embodiment, PGL can be included as a component of other antifreeze solutions used for plant frost protection. For example, PGL of suitable molecular weight might be used instead of other polymers as the thickening agent of the invention in U.S. Pat. No. 5,653,054.

Solutions containing PGL compounds are expected to exhibit a cleansing action against INAs, adhering to INAs so that INAs will be washed off surfaces, eventually depleting the surfaces of INA material. It has even been suggested that INA binding agents might exhibit a specific bactericidal activity against INA bacteria by blocking bacterial cell wall transport channels (U.S. Pat. No. 4,484,409—herein incorporated in its entirety by reference thereto).

Beyond agriculture, it is anticipated that the present invention will be broadly useful for preventing the freezing of water at temperatures a few degrees below freezing. PGL compounds may have utility as non-colligative antifreeze agents in a variety of industrial settings where it is desirable to inhibit the freezing of water, and permissible to add small quantities of solute. PGL compounds may be especially useful for inhibiting freezing of water which is present in small quantities as a contaminant in hydrophobic fluids, such as fuels. In this embodiment, the PGL compound would be formulated with a hydrophobic group rendering the molecule soluble in the hydrophobic fluid, but still capable of partitioning into the water phase to inhibit ice formation. The compound would also be suitable for use as an adjuvant in cryosurgery, in which maximization of supercooling prior to freezing maximizes the likelihood of intracellular ice formation upon freezing and, consequently, cell death. Another application could be improvement of traditional colligative "antifreeze" solutions such as automotive "antifreeze". Antifreeze solutions are typically rated to provide freezing protection down to a temperature equal to the freezing point of the solution. However this generally understates the protective potential of antifreeze solution because significant supercooling of the solutions can and does occur. The addition of PGL compounds to conventional antifreeze solutions would allow supercooling to occur more reliably and to deeper temperatures than ordinarily occurs. This would provide a greater margin of safety in freeze protection. This would benefit antifreeze solutions (such as engine coolant antifreeze and deicing solutions (keeping surfaces ice free linger after deicing).

The most obvious instance of solutions in which supercooling promotion would be beneficial is traditional colligative 'antifreeze' solutions such as automotive 'antifreeze'. Antifreeze solutions are typically rated to provide freezing protection down to a temperature equal to the freezing point of the solution. However this generally understates the protective potential of antifreeze solutions because significant supercooling of the solutions can and does occur. The addition of PGL compounds to conventional antifreeze solutions would allow supercooling to occur more reliably and to deeper temperatures than ordinarily occurs. This would provide a greater margin of safety in freeze protection. This would benefit antifreeze solutions (such as engine coolant antifreeze) and deicing solutions (keeping surfaces ice free longer after deicing).

Other uses for facilitating supercooling of aqueous solutions can also be contemplated. Any water-based product that can be harmed by freezing during either storage or use will benefit from the addition of non-colligative antifreeze compounds. For example, products that may be exposed to cold during a curing process will benefit from the additives of this invention. More specifically, water-based paints can be protected against freezing during either storage or drying by small amounts of PGL. Setting cement and concrete can also be protected against freezing by these additives.

Cryopreservation of biological material by vitrification is an extreme example of supercooling. Large concentrations of colligative solutes (cryoprotectants) are used to make preservation solutions with freezing points below −20° C. By cooling rapidly it is then possible to supercool these vitrification solutions to below −120° C. with no ice formation. At temperatures below −110 to −135° C. the supercooled solution undergoes a transition to a glassy solid, and is said to be "vitrified".

The supercooling ability of vitrification solutions is sensitively dependent upon cryoprotectant concentration. A critical cryoprotectant concentration, denoted Cvit, is necessary to successfully supercool without ice formation at a given cooling rate. The toxicity of vitrification solutions is also sensitively dependent upon concentration, often rising non-linearly as $C_{vit}$ is approached. Means to reduce $C_{vit}$ by even a few percent are therefore extremely valuable. Inhibition of background INAs in vitrification solutions by PGL offers the opportunity to achieve this.

The preservation of tissues and organs at hypothermic temperatures (temperatures near 0° C.) for several hours or days is also an active area of interest in cryobiology. One approach to hypothermic preservation involves maintaining organs in a supercooled state at temperatures slightly below the freezing point (Conn Med 59, pp. 387–99, 1995—herein incorporated in its entirety by reference thereto). Supercooled states are inherently at risk of freezing. The inclusion of ice nucleation inhibiting compounds of the present invention in supercooling preservation solutions reduces this risk, expanding the frontiers of this field. We have also found that PGL can be used for tissue slice preservation in place of a more permeable component (glucose) in a conventional 0° C. organ flush/cold storage solution without detrimental effects, implying potential utility of PGL for either storage below 0° C. or conventional storage at 0 to 10° C.

The binding affinity of the compounds of this invention for INAs makes it possible to contemplate systems designed to cleanse solutions of INAs instead of merely inhibiting them. In one embodiment, water or other aqueous solutions could be passed through columns (repeatedly, if necessary) containing high molecular weight and/or crosslinked PGL that is water insoluble. In another embodiment, the column material might contain a PGL compound as a covalent appendage on an insoluble resin or other substrate. It is anticipated that such columns would remove INAs from fluids passed through them by adsorption onto the PGL. In still another INA cleansing embodiment, a PGL compound would be introduced into the solution and then removed by exposure to material with a binding affinity for a ligand on the PGL molecule, or PGL itself. INA cleansing processes would be particularly useful for vitrification solutions, or solutions used for supercooled hypothermic preservation.

Environmental INAs play a pivotal role in initiating precipitation in the atmosphere. Inexpensive INA inhibitors such as PGL compounds may therefore also have utility for weather modification, as discussed in U.S. Pat. No 4,484,409 (herein incorporated in its entirety by reference thereto).

PGL and PVA appear to inhibit INAs in a complementary fashion, with each compound being optimum for inhibition of different classes of INAs. It is therefore expected that the optimum choice of INA-inhibiting agent may depend on the application, and that the best general-purpose formulation for ice inhibition will consist of a mixture of PVA and PGL compounds.

"The reason for the effectiveness of PGL as an antinucleator and an enhancer of the thermal hysteresis effect of antifreeze proteins is still not clear. We presume that the effect requires hydrogen bonding involving the OH groups in the molecule, particularly those in the middle portion of the molecule, and it remains possible that the oxygen links in the backbone of the molecule contribute to the antinucleation efficacy as well. Therefore, variants of PGL in which one or both of the terminal OH groups are deleted are likely to also be effective, particularly if the chain length involves at least six (6) glycerol monomer units, so that the number of available OH groups remains equivalent to the number of the OH groups present on tetraglycerol, which is effective as an antinucleator. Except for the hydrogens present in the OH groups in the molecule, the other hydrogens may be replaced judiciously with other atoms or groups to a limited extent (e.g., 10% replacement) without abolishing the activity of PGL. Generally, molecules of the form ($R_a$[—$OCR_2CROHCR_2$—]$_n R_b$), where R groups need not be the same at different sites in the molecule and where R, $R_a$ and $R_b$ are H, OH, $C_1$ to $C_6$ alkoxy or amino are effective for the applications described in this specification."

Additional explanation of the invention and description of best mode uses is contained in the following Examples.

EXAMPLES

Example 1

The first example of the use of PGL to enhance supercooling was its use as an additive in cryoprotectant solutions stored in a household refrigerator freezer compartment at about minus 20 degrees C. for several days (FIG. 1). The cryoprotectant used (Veg) is a mixture of DMSO and formamide in a 1:1 mole ratio (equivalent to a 1.732 to one weight ratio of dimethyl sulfoxide to formamide), to which is added ethylene glycol at a ratio of 1 gram of ethylene glycol per 2.27 grams of (DMSO+formamide). The vehicle solutions used were RPS-2 (a solution described in the scientific literature that contains 180 mM glucose [for full formula see, for example, G. M. Fahy et al., Chapter 20, in "Cell Biology of Trauma" (J. J. Lemasters and C. Oliver, Eds.), CRC Press, Boca Raton, Fla., 1995, pp. 333–356]) or RPS-T (a solution identical to RPS-2 but containing 5 mM glucose and 175 mM trehalose in place of the glucose subtracted from RPS-2). The solutions containing RPS-2 did not show enhanced supercooling ability with decaglycerol (dG). The solutions were composed of 22% w/v to 33% w/v Veg with or without the inclusion of 1% w/v decaglycerol (PGL for which n=10 monomer units, abbreviated as dG) or 0.5% w/v dG plus 0.5% PVA (abbreviated as X1000 in the figure legend). In the absence of dG, 30% w/v Veg was required to prevent freezing of the samples, all samples of either 28% w/v Veg in RPS-2 or 28% w/v Veg in RPS-T reverting to the frozen state. The inclusion of 1% w/v dG in the RPS-T-based Veg solutions permitted long-term stable supercooling of 23% w/v Veg, and a mixture of 0.5% w/v dG and 0.5% w/v X1000 permitted stable supercooling of a 22% w/v Veg solution in the same vehicle. Thus, dG, alone or in combination with PVA, reduced the concentration needed for supercooling by 6–7% w/v. Assuming a critical concentration without dG of about 29% w/v, this represents a relative reduction of up to 100%×7/29=24%. Furthermore, and surprisingly, these supercooled solutions remained unfrozen even after vigorous shaking, an action that normally induces freezing almost immediately in strongly supercooled solutions. The figure also shows, however, that this level of protection was not seen when the vehicle was RPS-2, 22 and 23% w/v Veg solutions freezing spontaneously even in the presence of 1% dG or the combination of dG and PVA. Since the only difference between RPS-2 and RPS-T is the higher concentration of glucose in RPS-2, it is apparent that dG and the combination of dG and PVA are best used to enhance supercooling in solutions containing less than 180 mM glucose. The sample volume in these experiments was approximately 15 ml.

Example 2

Figure 2:
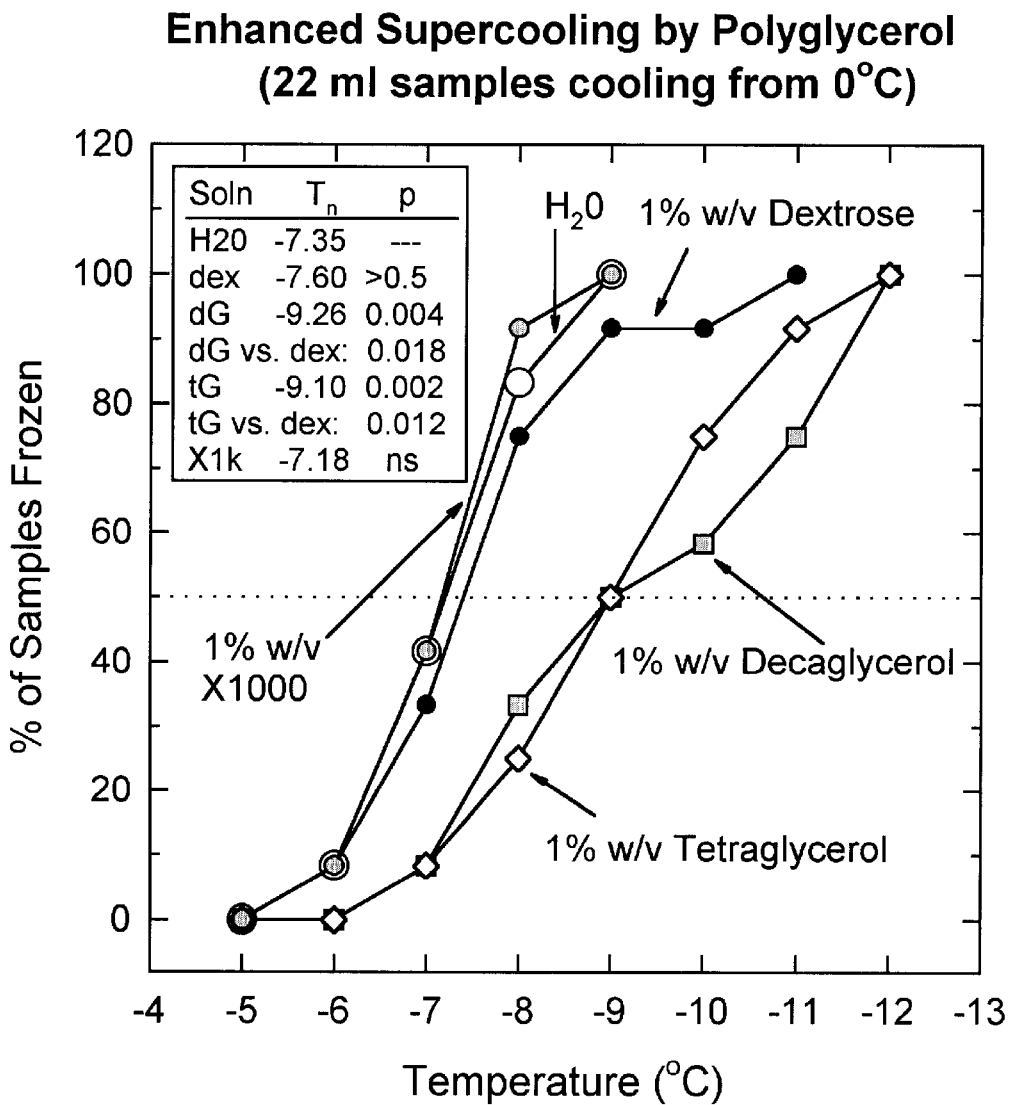
FIG. 2 shows statistically significant non-colligative depression of the mean freezing point of water by tetraglycerol and decaglycerol in 22 ml samples frozen cooled very slowly from 0° C. by being placed in a large, slowly-cooling bath of 60% v/v ethylene glycol.

FIG. 2 shows the nucleation spectrum of nucleators present in individual ~20 ml samples of pure laboratory water (purified by reverse osmosis and deionization but not by distillation) as modified by PVA, dG, and tetraglycerol (tG, a PGL polymer comprising 4 glycerol monomers). In this example, the PVA addition (X1000 ice blocker, available from 21$^{st}$ Century Medicine, Rancho Cucamonga, Calif. 91730) was without effect, whereas dG and tG provided statistically significant improvements (p=0.004 to 0.018 and p=0.002 to 0.012, respectively) in the mean nucleation temperature (Tn) of pure water or 1% dextrose in water as a further control. Further, the non-colligative nature of the Tn depression achieved is evident from the failure of 1% dextrose, which is more colligatively active than a higher molecular weight polymer, to substantially reduce Tn. In this experiment, 12 samples of each solution were cooled slowly and the number of samples frozen at each degree below 0 was counted and converted to the format shown above.

Example 3

Figure 3:
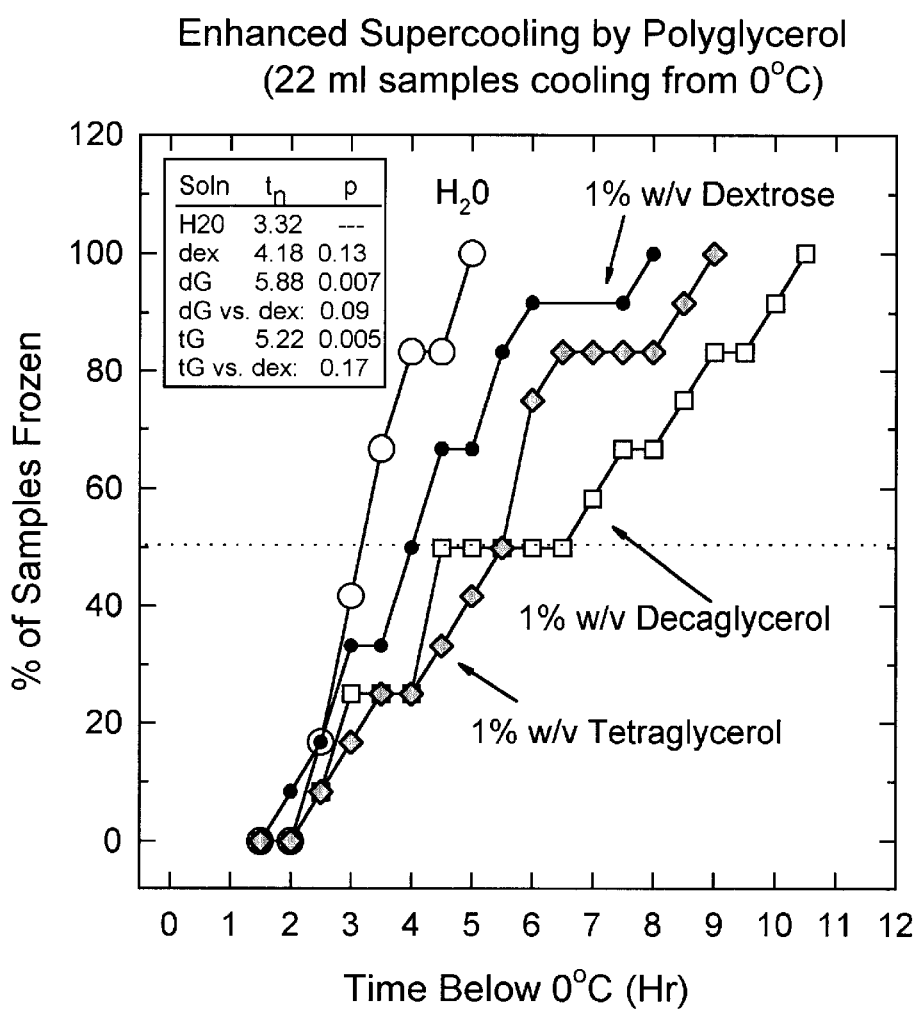
FIG. 3 expresses the data of FIG. 2 in terms of the time required for nucleation to occur during very slow cooling from 0° C., showing statistically significant extension of the man time to nucleate compared to pure water, as opposed to a lack of significant extension of time by a dilute colligative agent (dextrose).

In this example (FIG. 3), the data of Example 2 are expressed in terms of the time required for nucleation to occur. Both decaglycerol and tetraglycerol statistically significantly delayed the onset of nucleation. In an environmental context, such slowing could allow plants to remain supercooled until the temperature rises with the rising sun.

Example 4

Figure 4:
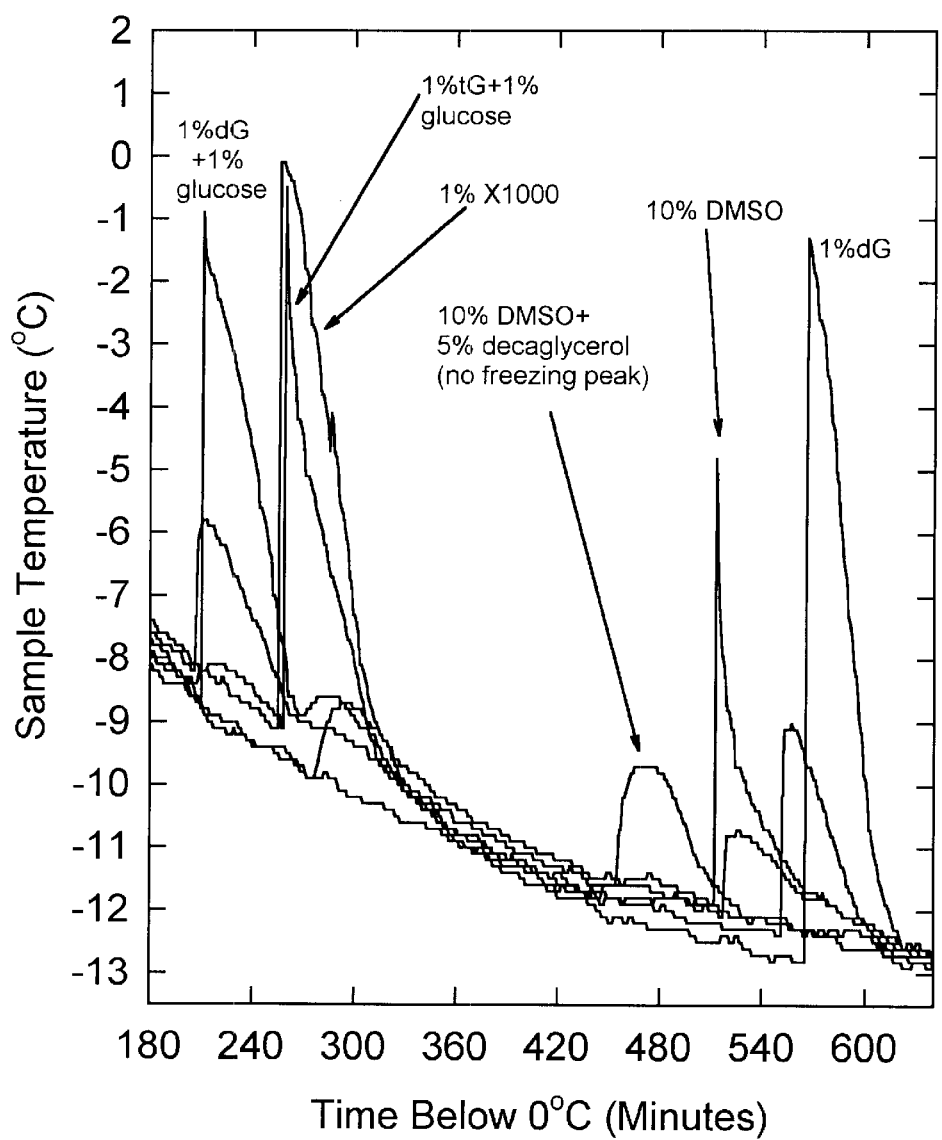
FIG. 4 compares nucleation temperatures for individual samples cooling very slowly from 0° C., showing profound supercooling with 1% decaglycerol, elimination of this effect by 1% dextrose, and the prevention of freezing of 10% DMSO by 5% decaglycerol down to −13° C.

Solutions composed of ~20 ml of water containing one of six different additives or additive combinations as indicated in FIG. 4 were cooled together and nucleation of each sample was detected by the presence of a sudden exotherm recorded by continuous computer monitoring of a fine thermocouple placed in each sample container. The cooling rate was similar to that in Examples 2 and 3. Consistent with Example 1 above, samples with 1% (15 mM) dextrose+1% dG, 1% dextrose+1% tG, and with 1% X1000 alone froze at higher temperatures, whereas, the sample of 1% dG in water froze at a temperature lower than a sample containing 10% DMSO (the thermodynamic freezing/melting point of the latter sample is above about −3° C.). Addition of 5% dG to 10% DMSO prevented freezing of 10% DMSO down to the lowest temperature reached in this experiment (−13° C.).

(The minor upward temperature excursions are induced by freezing of neighboring samples; major upward temperature excursions are signatures for the freezing of the sample containing the probe used to make the recordings. The peak labeled '10% DMSO+5% decaglycerol' resulted from the freezing of a nearby extraneous sample whose thermal history is not included in the graph for the sake of simplicity.

In this and similar runs, some nucleation may be induced by the temperature probes, thus underestimating the antinucleation potential of the polyglycerols).

Example 5

Figure 5:
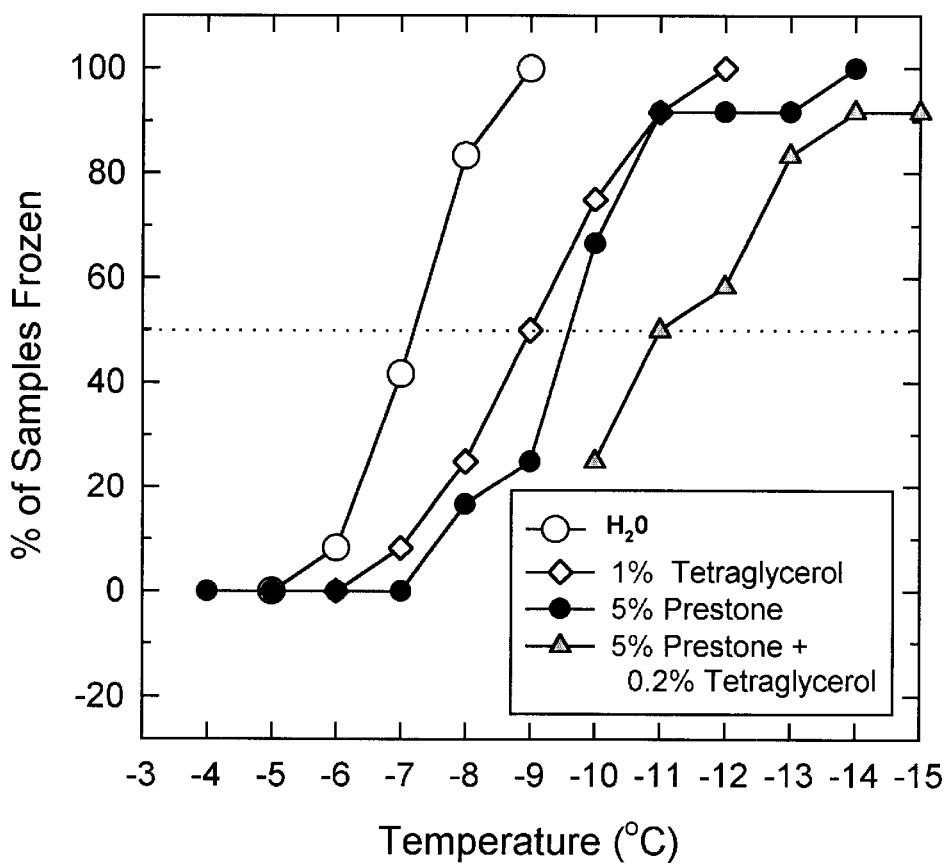
FIG. 5 shows comparability of supercooling in 5% v/v automobile antifreeze and in 1% w/v tetraglycerol, and improvement in supercooling of 5% v/v automobile antifreeze by the addition of 0.2% w/v tetraglycerol.

In this example (FIG. 5), ~20 ml samples were cooled similarly to the samples in Examples 2–4. 1% tetraglycerol was nearly equivalent to 5% v/v commercial PRESTONE™ antifreeze in inhibiting nucleation, and 0.2% w/v tetraglycerol reduced the probability of nucleation of 5% v/v PRESTONE™ at temperatures below −9° C.

Example 6

Figure 6:
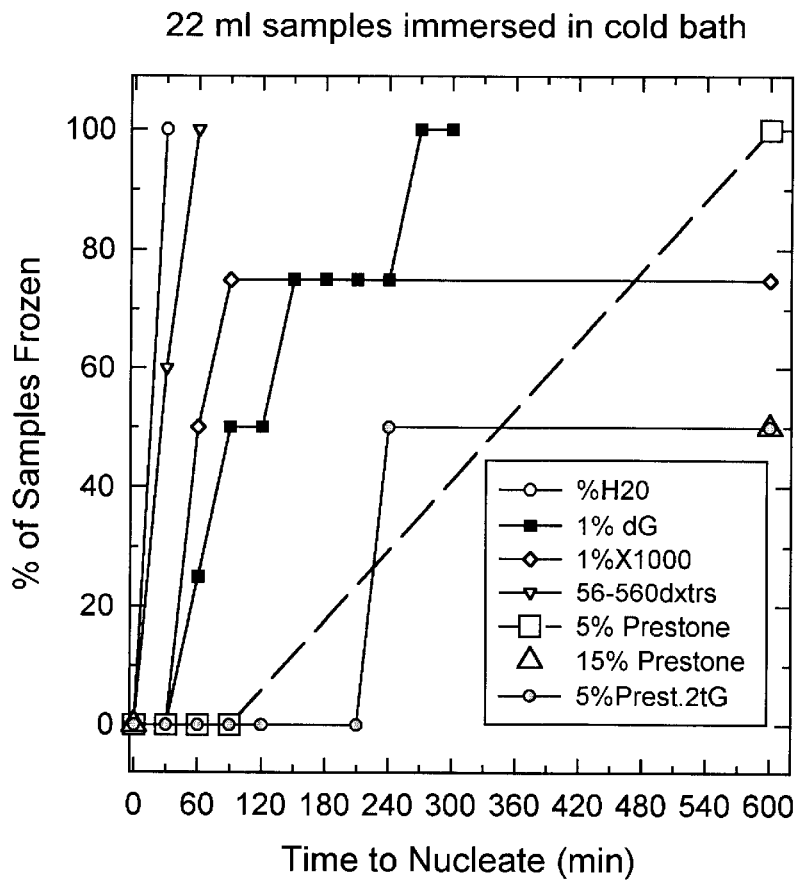
FIG. 6 shows that the likelihood of freezing of 5% v/v automobile antifreeze after 10 hours of cooling (100%) can be made equivalent to the likelihood of freezing of 15% v/v antifreeze (50%) by the addition of 0.2% w/v tetraglycerol.

FIG. 6 is a further example of stabilization of PRESTONE™ antifreeze, based on direct immersion of PRESTONE™ samples into a low temperature bath, with scoring based on the time required for the samples to freeze within the first 300 minutes or on the cumulative probability of freezing after 600 minutes (the samples were not observed between 300 and 600 minutes). In this example, a higher percentage of samples failed to freeze upon cooling overnight to about −14.6 degrees C. than in Example 5, perhaps due to nucleation from the thermocouple probes in Example 5.

The light dotted line in FIG. 6 represents 56 or 560 mM dextrose control solution. X1000 again refers to the PVA/PVA polymer referred to earlier in the text. Note that in this example, the probability of freezing of 5% PRESTONE™ could be made the same as the probability of freezing of 15% v/v PRESTONE™ after cooling all night to about −14.6 degrees C. by the addition of only 0.2% w/v tetraglycerol to the 5% PRESTONE™.

Example 7

Veg (55% w/v Veg solutes [see U.S. patent application Ser. No. 09/400,793]) is a non-toxic solution of cryoprotectants than is unable, by itself, to vitrify. Addition of 1% dG to this solution does not allow it to vitrify in the presence of RPS-2 (180 mM glucose present). However, addition of 0.5% dG plus 0.5% X1000 to Veg in an RPS-T vehicle allowed it to vitrify upon cooling at 10 degrees C. per minute and to virtually escape devitrification on warming at about 60 degrees C. per minute. This solution is expected to yield ≧90% cellular viability in kidney slices.

Example 8

The inability of Veg to vitrify in RPS-T alone was overcome by a modification of RPS-T that is the subject of a separate patent application. Adding 0.5% dG and 0.5% X1000 to 2X RPS-T reduced the concentration of Veg needed to vitrify down to a total of 52% w/v Veg. This is expected to yield good cellular survival. This is a further example of another context in which the antinucleation properties of PGL have been demonstrated.

Example 9

Figure 7:
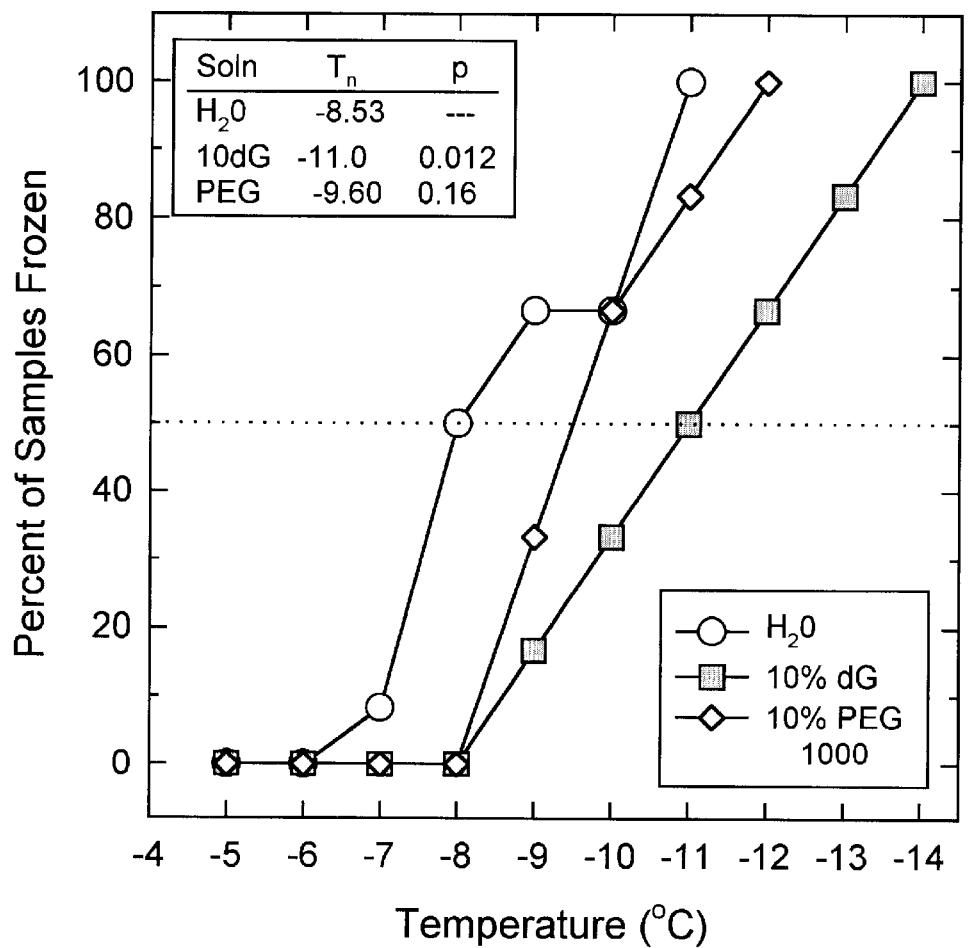
FIG. 7 shows statistically significant ($p=0.012$) depression of the mean nucleation temperature (Tn) of water by 10% w/v crude decaglycerol (9% w/v actual decaglycerol concentration) vs. the failure of a comparable polymer to significantly depress Tn, when test solutions were immersed in a bath precooled to −15° C.

FIG. 7 compares the antinucleation activity of 10% w/v dG to that of 10% w/v polyethylene glycol of mean molecular mass ~1000 daltons (PEG 1000). Decaglycerol produced a statistically significant reduction in mean nucleation temperature in comparison to water, but PEG 1000 did not, despite the fact that the molecular mass of PEG 1000 is similar to that of dG(~750 daltons), further indicating the uniqueness of dG.

Example 10

Figure 8:
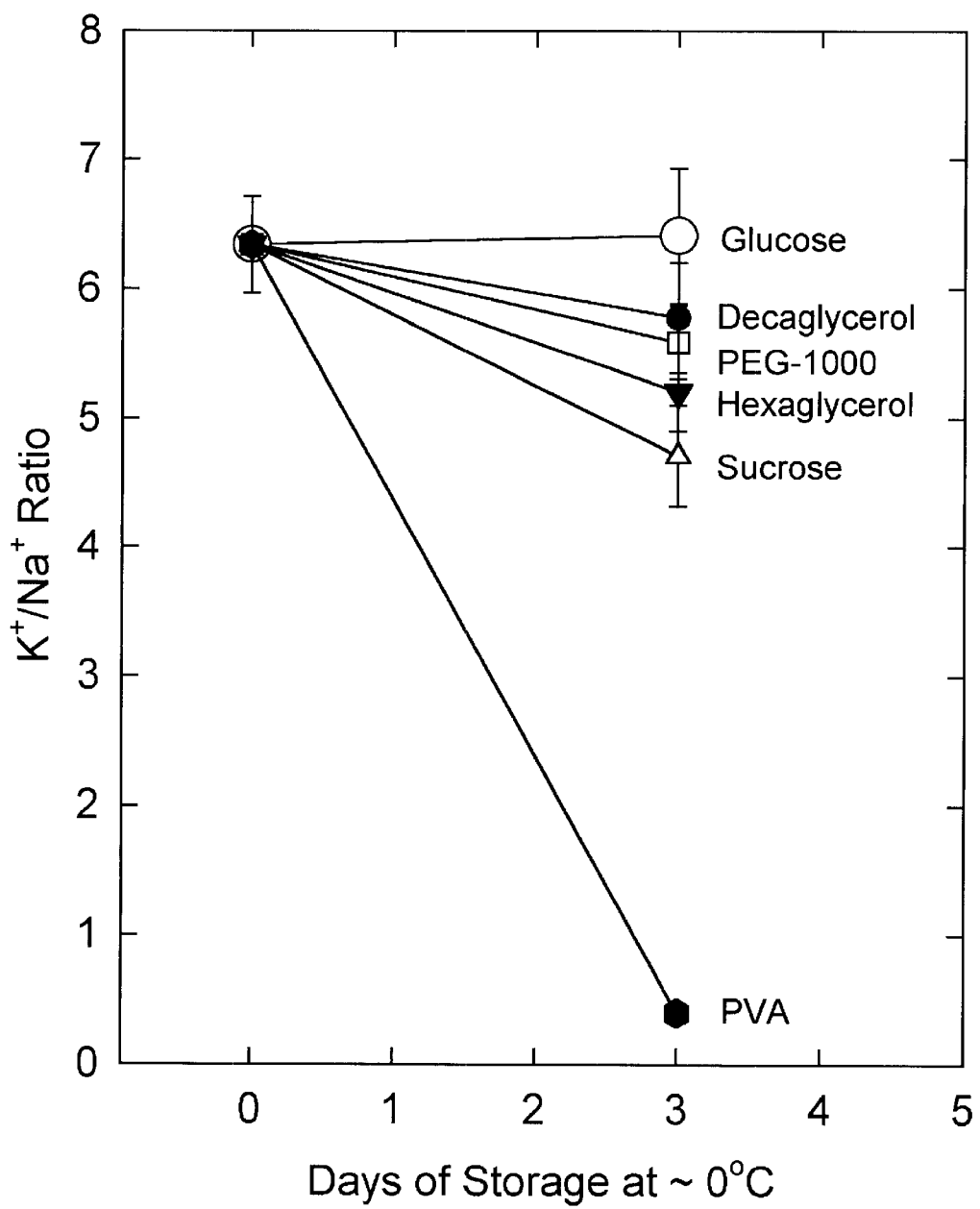
FIG. 8 shows the lack of toxicity of PGL as used in an organ preservation solution in place of glucose for preservation of kidney slices.

RPS-2 is an excellent solution for static (non-perfusional) storage of kidney slices and whole rabbit kidneys (see for example Khirabadi and Fahy, Cryobiology 30: 10–25, 1994). As shown in FIG. 8, kidney slices stored in RPS-2 (curve labeled "Glucose", open circles) could be stored for 3 days near zero degrees C. with no demonstrable deterioration based on their subsequent ability to accumulate potassium and to extrude sodium during incubation in Cross-Taggart solution (see Fahy et al., in "Cell Biology of Trauma", J. J. Lemasters and C. Oliver, Eds., CRC Press, 1995, pp. 333–356, and citations therein, for the precise methodology of the functional assay). RPS-2 contains 180 mM glucose as a major component. When 170 mM glucose was replaced with an osmotically equivalent amount of decaglycerol (Black circles, curve labeled "decaglycerol"), the slices were preserved as well or nearly as well as with glucose. This modification may make the solution applicable to organs such as the liver, whose cells are too permeable to glucose to allow the use of RPS-2 for ideal preservation. It may also protect organs during cooling, warming, and holding (for example, during transplantation) at temperatures that are high enough (>5° C.) to allow rapid enough glucose transport to be a concern for cell swelling. The modification may also allow the solution to be used with improved results for perfusion as opposed to static storage. Furthermore, inclusion of PGL in place of some glucose in RPS-2- or Euro-collins-like vehicle solutions may facilitate the vitrification of solutions and therefore of cells, tissues, and organs containing cryoprotectants in view of the antinucleation effects of PGL. Hexaglycerol (inverted black triangles) was nearly as good as decaglycerol, and the difference in results was associated with formation of a precipitate in the hexaglycerol solutions that could probably be avoided by adjusting the concentrations of calcium, phosphate, and/or bicarbonate without adverse effects. Polyethylene glycol of mean molecular mass ~1000 daltons (PEG-1000, open boxes) also yielded excellent results, whereas sucrose (open triangles) was distinctly worse than glucose, and PVA (black hexagons) was directly toxic at a concentration of ~170 milli-osmolal. Any concentration of decaglycerol, PEG-1000, and hexaglycerol between 0 and 170 mOsm should give ion transport results equal to or superior to those shown. It is expected that PGL containing 3–5, 7–9, and >10 glycerol monomers will also be effective. The example of FIG. 8 underscores the lack of toxicity of even high concentrations of PGL.

Example 11

Figure 9:
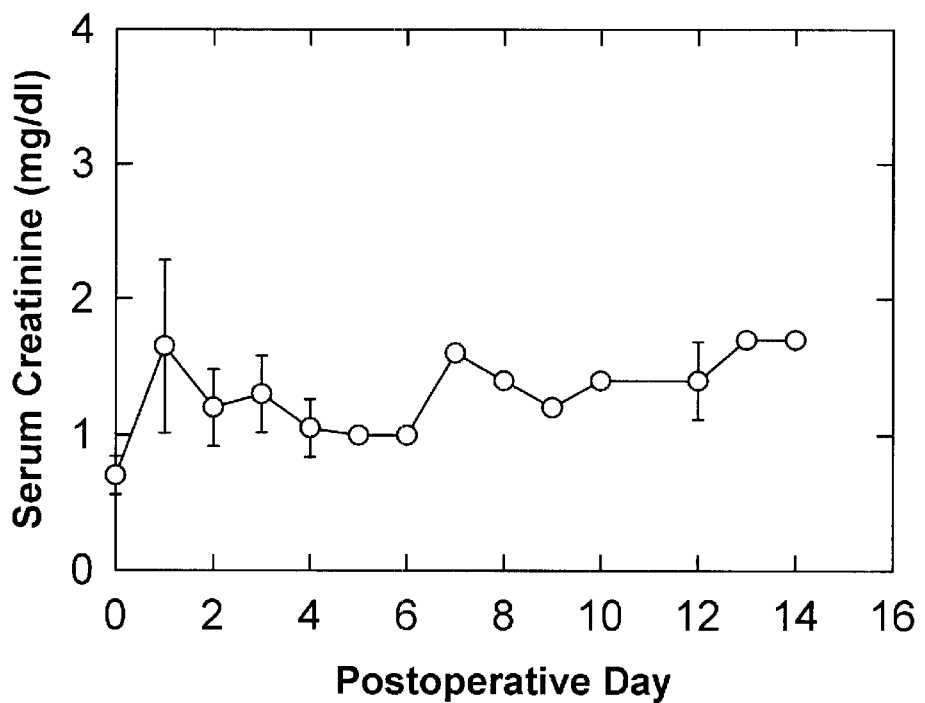
FIG. 9 shows the lack of toxicity of PGL used in a perfusate employed for the preservation of whole kidneys.
Figure 10:
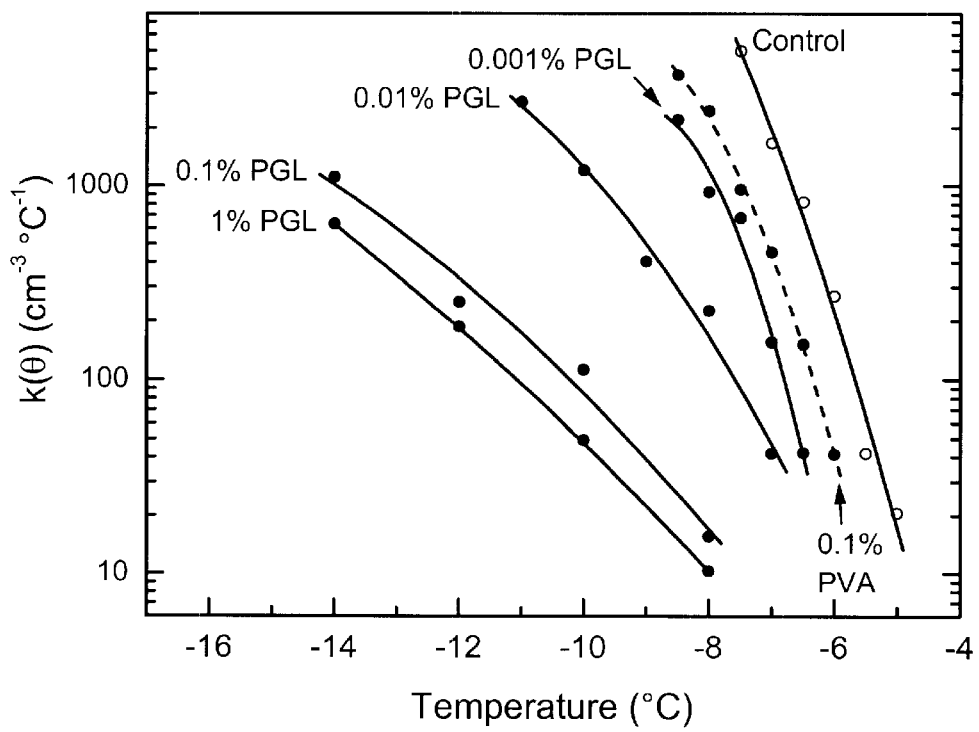
FIG. 10 shows the differential ice nucleator spectra for various concentrations of PGL and PVA in water containing 1 ppm *P. syringae* ice-nucleating bacteria, showing inhibition of bacterial nucleators by PGL.
Figure 11:
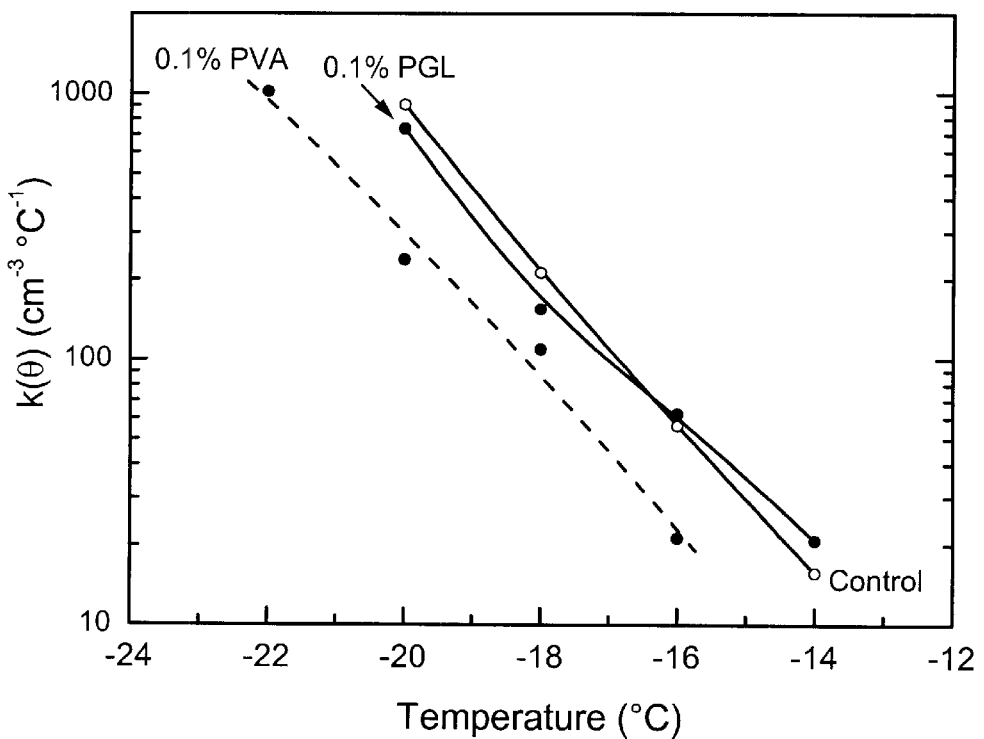
FIG. 11 shows the differential ice nucleator spectra for a sample of water drawn from the surface of Lake Elsinore, Calif., in the presence and absence of 0.1% w/w PVA or PGL, and shows the comparatively weak effect of PGL for this sample.

Two kidneys were perfused for 5 hours at about 3.5 degrees C. with an RPS-2-like solution that contained 1% w/v decaglycerol in addition to other components. The kidneys were transplanted, and their recovery was measured by the postoperative serum creatinine levels attained. As indicated in FIG. 9, the postoperative functional recovery of these kidneys was good, showing the lack of toxicity of PGL for the vascular system and the applicability of PGL for use in perfusates, including perfusates containing cryoprotectants that are made to vitrify with the assistance of the included PGL.

Example 12

The ability of PGL to act in concert with naturally-occurring antinucleators and ice crystal growth inhibiting proteins was also studied and confirmed. PGL increased the thermal hysteresis activity of 1% w/v recombinant *Dendroides canadensis* antifreeze protein (dAFP-1; described in detail in Biochemistry 37: 6343–6350, 1998, and J. Comp. Physiol. [B] 168: 225–232, 1998, and listed in Genbank, for example) from an expected value [see FIG. 1 of U.S. Pat. No. 5,627,051] of 1.5° C. without PGL to 3.5° C. with PGL, as determined by cryomicroscopic observation of 0.2 microliter samples surrounded by 1.6 microliters of mineral oil on the stage of a Linkam BCS 196 cryomicroscope. In these experiments, the dAFP solution was frozen by cooling to −30° C. and warmed to just below the thermodynamic melting point of the solution, and then cooled slowly until spontaneous rapid growth of ice in the solution was observed. Thermal hysteresis was defined as the highest temperature at which ice could exist (the melting point) minus the highest temperature at which small amounts of ice existing in the presence of the protein were able to rapidly grow (the freezing point).

A sample consisting of 1% w/v natural dAFP-1 plus 1% w/v decaglycerol was found to have a thermal hysteresis of 2.4° C. whereas 1% w/v dAFP-1 alone yielded thermal hysteresis values of 0.9 to 1.1° C. at the most, a 2% w/v sample of mixed dAFP-1 and dAFP-2 had a thermal hysteresis of only 1.5° C.

In these experiments, the dAFP solution was frozen by cooling to −30° C. and warmed to just below the thermodynamic melting point of the solution, and then cooled slowly until spontaneous rapid growth of ice in the solution was observed. Thermal hysteresis was defined as the highest temperature at which ice could exist (the melting point) minus the highest temperature at which small amounts of ice existing in the presence of the protein were able to rapidly grow (the freezing point). PGL appeared to work at least in part by preventing extraneous nucleation. This allowed the observed thermal hysteresis to be broken by growth of the pre-existing ice to which the dAFP had already bonded rather than by rapid growth of new ice that had not had time to be bonded by AFP.

Thus, the anitnucleation ability of PGL can allow antifreeze proteins to be far more effective at preventing ice formation in situations in which some ice has previously formed by has become inactivated by the antifreeze protein.

Example 13

INAs are ubiquitous in nature, and are known to be of both mineral and biological origin (Vali, G. in Biological Ice Nucleation and Its Applications, eds Lee, R. E., Warren, J. W. & Gusta, L. V., pages 1–28, APS Press, St. Paul, Minn., 1995). Proteinaceous INAs of bacterial origin are particularly potent, and are believed to be primarily responsible for nucleation of ice near 0° C. in natural settings. It is shown here that polyglycerol and polyvinyl alcohol are able to inhibit INAs of the ice nucleating bacterium *Pseudomonas syringae* in a manner similar to antifreeze proteins (AFPs) and antifreeze glycoproteins (AFGPs).

Polyglycerol is particularly effective, reducing the mean freezing temperature in the presence of *P. syringae* by as much as 6° C. Interestingly, only polyvinyl alcohol was effective at inhibiting INAs in an environmental water sample. These results support the existence of separate classes of INAs in nature, and suggest that the inhibitory action of polyvinyl alcohol and polyglycerol are complementary. The availability of simple and inexpensive INA inhibitors has important implications for agriculture and biological cryopreservation. Inhibition of natural INAs by common hydrophilic polymers has not been demonstrated previously.

Bacterial INA solutions were prepared by adding one part per million (by weight) freeze-dried *Pseudomonas syringae* 31*A*(Snomax®, York International, Victor, N.Y.) to ultrapure lab water. The differential nucleator spectrum, k(θ), of the solution (Control curve of FIG. 10) was determined by measuring the distribution of freezing temperatures in a population of 1 μL drops (Vali, G. in Biological Ice Nucleation and Its Applications, eds Lee, R. E., Warren, J. W. & Gusta, L. V., pages 1–28, APS Press, St. Paul, Minn., 1995; and Vali, G. Quantitative evaluation of experimental results on the heterogeneous freezing nucleation of supercooled liquids. *J. Atmos. Sci.* 28, pages 402–409, 1971).

Differential nucleator spectra were obtained by the drop freezing assay of Vali (Vali, G. in Biological Ice Nucleation and Its Applications, eds Lee, R. E., Warren, J. W. & Gusta, L. V., pages 1–28, APS Press, St. Paul, Minn., 1995). Seven 1μL drops were dispensed with a Hamilton microliter syringe into an aluminum sample pan (Perkin Elmer 0219-0041) and covered with mineral oil to reduce evaporation. The open sample pan was placed inside the oven of a Perkin Elmer DSC 7 differential scanning calorimeter, and the sample was cooled at 2° C./minute until all drops were frozen. The freezing temperature of each drop was recorded from its peak on the thermogram. Freezing data for a population of 98 drops (14 sample pans) were obtained to determine each spectrum. Spectra were computed by the formula $$k(\theta)=-(1/V\Delta\theta)\ln[1-\Delta N/N(\theta)],0$$

where V is the drop volume (1 μL), N(θ) is the number of unfrozen drops at temperature θ, and ΔN is the number of drops observed to freeze in the temperature interval Δθ. Nucleation by causes extrinsic to the solutions tested was ruled out by observing that samples of ultrapure lab water (Milli-Q Biocel) did not freeze at temperatures above −20° C. Polyglycerol (PGL) of $M_r$ ~750 was added to the bacterial INA solution in concentrations up to 1% by weight. The resulting nucleator spectra are shown in FIG. 10. The mean freezing temperature was lowered from −6.8° C. (control) to −8.0, −9.4, −12.5, and −13.4° C. for 0.001%, 0.01%, 0.1% and 1% PGL concentrations respectively. Polyvinyl alcohol (PVA) of $M_r$ ~1500 (80% hydrolyzed, also known as X1000) was also tested at 0.1% concentration, and found to exhibit significant nucleation inhibition (FIG. 10). The water-soluble polymers polyvinyl pyrrolidone ($M_r$ 5000), polyethylene glycol ($M_r$ 1000), polyacrylamide ($M_r$ 1500), and dextran ($M_r$ 40000) were also tested at 0.1% concentration and found to have no effect on the nucleator spectrum.

Nucleator spectra were also obtained for a sample of natural lake water (FIG. 11). The INAs present in this sample were inhibited by PVA, but were comparatively unaffected by PGL. This implies that PVA and PGL act largely against different nucleator classes, and that differential sensitivity of nucleation to inhibition by PGL and PVA can be a useful and novel method for characterizing INAs that is independent of previous classification schemes that rely on temperature-sensitivity only (Turner, M. A., Arellano, F. & Kozloff, L. M. Three separate classes of bacterial ice nucleation structures. *J. Bacteriol.* 172, 2521–2526 , 1990). However, the nucleators found in lake water became active only below −14° C., whereas the anti-nucleator activity of PGL for *P. syringae* nucleators was greatly reduced in FIG. 8 near −14° C. To determine whether the antinucleation effect of PGL is limited more by temperatures below −14° C. or by specific nucleator class, a one part per billion solution of freeze-dried *P. syringae* was prepared, reducing the mean nucleation temperature to −15° C. The inefficient *P. syringae* nucleators remaining in this dilute solution were still inhibited by PGL, indicating that it is the nature of the INAs, not the nucleation temperature per se, that determines PGL-sensitivity.

These observations collectively confirm the Examples given earlier showing activity of PGL at temperatures ranging from 0° C. to −23° C. in macroscopic samples containing very low background concentrations of nucleators.

Example 14

Figure 12:
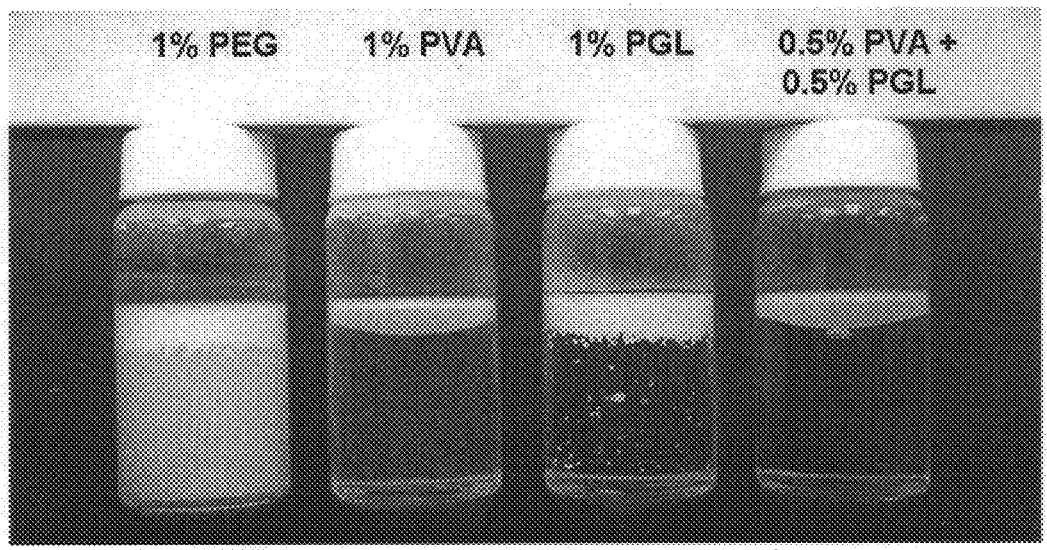
FIG. 12 demonstrates complementary and additive inhibition of nucleation in 55% w/w aqueous ethylene glycol supplemented with bacterial nucleator, and indicates that the combination of (polyvinyl alcohol)/(polyvinyl acetate) copolymer (PVA) and polyglycerol can allow vitrification of a solution that neither agent alone can allow to vitrify at the same total concentration.

Deep supercooling in the presence of colligative cryoprotectants can result in solution vitrification, which has been proposed as a means of cryopreserving complex tissues without damage from ice (Fahy, G., MacFarlane, D., Angell, C. & Meryman, H. Vitrification as an approach to cryopreservation. *Cryobiology* 21, 407–426, 1984). Toxicity of the high cryoprotectant concentrations required for vitrification remains an obstacle to application in many large systems of interest, such as transplantable organs (Fahy, G. M., Saur, J., and Williams, R. J. Physical problems with the vitrification of large biological systems. *Cryobiology* 27, 492–510, 1990). FIG. 12 demonstrates simultaneous complementary inhibition of *P. syringae* nucleator subpopulations by PVA and PGL under conditions similar to those used for cryopreservation by vitrification. Inhibition of background INAs by these polymers can similarly reduce the cryoprotectant concentrations required to achieve vitrification of biological systems.

What is claimed is:

1. A method of promoting the ability of a cell or tissue preservation solution to be used to preserve biological material in a supercooled state of temperatures below 0° C., comprising adding ice inhibiting molecules to the solution, said molecules having the following formula:

$(R_a[\text{—}OCR_2CROHCR_2\text{—}]_nR_b)$ where R, $R_a$ and $R_b$ are H, OH, $C_1$ to $C_6$ alkoxy or amino and wherein n is about 2 to about 1000.

2. An ice inhibiting molecule having the following formula:

$(R_a[\text{—}OCR_2CROHCR_2\text{—}]_nR_b)$ where R, $R_a$ and $R_b$ are H, OH, $C_1$ to $C_6$ alkoxy or amino and wherein n is about 2 to about 1000 wherein said molecule is covalently bonded to a hydrophobic group, and wherein the added hydrophobic group renders the molecule soluble in a hydrophobic solvent.

3. A method of preventing the freezing of water impurities in a hydrophobic fluid, comprising adding ice inhibiting molecules to said fluid, said molecules having the following formula:

$(R_a[\text{—}OCR_2CROHCR_2\text{—}]_nR_b)$ where R, $R_a$ and $R_b$ are H, OH, $C_1$ to $C_6$ alkoxy or amino and wherein n is about 2 to about 1000.

4. A method of inhibiting the ice forming tendency of ice nucleating bacteria and the proteins said bacteria produce comprising adding ice inhibiting molecules to surfaces or solutions containing said bacteria, said molecules having the following formula:

$(R_a[\text{—}OCR_2CROHCR_2\text{—}]_nR_b)$ where R, $R_a$ and $R_b$ are H, OH, $C_1$ to $C_6$ alkoxy or amino and wherein n is about 2 to about 1000.

5. A method of inhibiting the recrystallization of ice in a solution comprising adding ice inhibiting molecules to the solution, said molecules having the following formula:

$(R_a[\text{—}OCR_2CROHCR_2\text{—}]_nR_b)$ where R, $R_a$ and $R_b$ are H, OH, $C_1$ to $C_6$ alkoxy or amino and wherein n is about 2 to about 1000.

6. A method of removing ice nucleating agents from water or a water solution, comprising passing the water or water solution over or through an insoluble material, said material being bonded to molecules having the following formula:

$(R_a[\text{—}OCR_2CROHCR_2\text{—}]_nR_b)$ where R, $R_a$ and $R_b$ are H, OH, $C_1$ to $C_6$ alkoxy or amino and wherein n is about 2 to about 1000.

7. A method of preventing ice nucleation in supercooled water droplets in a rain cloud, comprising adding ice inhibiting molecules to the water droplets, said ice inhibiting molecules having the following formula:

$(R_a[\text{—}OCR_2CROHCR_2\text{—}]_nR_b)$ where R, $R_a$ and $R_b$ are H, OH, $C_1$ to $C_6$ alkoxy or amino and wherein n is about 2 to about 1000.

8. A method of promoting the ability of water to supercool, comprising adding ice inhibiting molecules to the water, said molecules having the following formula:

$(R_a[\text{—}OCR_2CROHCR_2\text{—}]_nR_b)$ where R, $R_a$ and $R_b$ are H, OH, $C_1$ to $C_6$ alkoxy or amino and wherein n is about 2 to about 1000, and further adding polyvinyl alcohol (PVA) ice inhibiting compounds.

9. A method of promoting the ability of water to supercool comprising adding ice inhibiting molecules to the water, said molecules having the following formula:

$(R_a[\text{—}OCR_2CROHCR_2\text{—}]_nR_b)$ where R, $R_a$ and $R_b$ are H, OH, $C_1$ to $C_6$ alkoxy or amino and wherein n is about 2 to about 1000.

10. The method of claim 9 in which $R_b$ is an OH.

11. The method of claim 9 in which $R_a$ is H and $R_b$ is an alkoxy.

12. The method of claim 9 in which the ice inhibiting molecules are polyglycerol (PGL).

13. The method of claim 12 in which the ice inhibiting molecules are selected from the group consisting of diglycerol, tetraglycerol, hexaglycerol and decaglycerol.

14. The method of claim 12 in which each PGL molecule has a molecular weight of about 166 to about 74,000 daltons.

15. The method of claim 12 in which each PGL molecule has a molecular weight of about 314 to about 758 daltons.

16. The method of claim 9 in which at least one of the hydroxyls is replaced by an ether or an ester group.

17. The method of claim 9 in which the ice inhibiting molecules are added in concentrations of about ten parts per million to about one part in ten.

18. The method of claim 9 wherein the water is on the surface of a plant.

19. The method of claim 9 wherein the water is inside a plant.

20. A method of promoting the ability of a water-containing solution to supercool, comprising adding ice inhibiting molecules to said water-containing solution, said ice inhibiting molecules having the following formula:

$(R_a[\text{—}OCR_2CROHCR_2\text{—}]_nR_b)$ where R, $R_a$ and $R_b$ are H, OH, $C_1$ to $C_6$ alkoxy or amino and wherein n is about 2 to about 1000.

21. The method of claim 20 wherein the ice inhibiting molecules are added to the water-containing solution in concentrations of about ten parts per million to about one part in ten.

22. The method of claim 20 wherein the water-containing solution is an antifreeze solution.

23. The method of claim 20 wherein the water-containing solution is a de-icing or frost prevention solution.

24. The method of claim 20 wherein the water-containing solution is water-based paint.

25. The method of claim 20 wherein the water-containing solution occurs in wet concrete.

26. The method of claim 20 wherein the water-containing solution is for biological preservation by vitrification.

27. The method of claim 26 wherein the ice inhibiting molecules are present in concentrations of about 0.1% to about 3%.

28. A cryoprotectant solution for cryopreservation by vitrification, comprising ice inhibiting molecules present in concentrations of about 0.1% w/v to about 3% w/v, wherein said ice inhibiting molecules have the following formula:

$(R_a[\text{---}OCR_2CROHCR_2\text{---}]_nR_b)$ where R, $R_a$ and $R_b$ are H, OH, $C_1$ to $C_6$ alkoxy or amino and wherein n is about 2 to about 1000.

29. A molecule for inhibiting ice formation and growth, said molecule having the following formula:

$(R_a[\text{---}OCR_2CROHCR_2\text{---}]_nR_b)$ where R, $R_a$ and $R_b$ are H, OH, $C_1$ to $C_6$ alkoxy or amino and wherein n is about 2 to about 1000.

* * * * *